United States Patent
Lysgaard et al.

(10) Patent No.: US 9,629,984 B2
(45) Date of Patent: Apr. 25, 2017

(54) MEDICAL BALLOON AND BALLOON CATHETER ASSEMBLY

(75) Inventors: Thomas Lysgaard, Solroed Strand (DK); Steen Aggerholm, St. Heddinge (DK); David A. Drewes, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 358 days.

(21) Appl. No.: 13/593,801

(22) Filed: Aug. 24, 2012

(65) Prior Publication Data
US 2013/0053770 A1 Feb. 28, 2013

(30) Foreign Application Priority Data

Aug. 25, 2011 (GB) .................................. 1114703.0

(51) Int. Cl.
| | |
|---|---|
| *A61M 29/00* | (2006.01) |
| *A61M 25/10* | (2013.01) |
| *A61L 29/04* | (2006.01) |
| *A61L 29/18* | (2006.01) |
| *A61M 25/01* | (2006.01) |
| *A61B 90/00* | (2016.01) |

(52) U.S. Cl.
CPC ............ *A61M 25/10* (2013.01); *A61L 29/04* (2013.01); *A61L 29/18* (2013.01); *A61M 25/0108* (2013.01); *A61M 25/1029* (2013.01); *A61B 2090/3925* (2016.02); *A61M 25/1027* (2013.01); *A61M 2025/1075* (2013.01); *A61M 2025/1079* (2013.01)

(58) Field of Classification Search
CPC .............. A61M 25/10; A61M 25/1027; A61M 25/1029; A61M 2025/1075; A61M 2025/1079
USPC ........................................ 604/103.01, 103.06
See application file for complete search history.

(56) References Cited

U.S. PATENT DOCUMENTS

| | | |
|---|---|---|
| 3,228,894 A | 1/1966 | Jeckel |
| 4,702,252 A | 10/1987 | Brooks et al. |
| | (Continued) | |

FOREIGN PATENT DOCUMENTS

| | | |
|---|---|---|
| WO | WO 03/037421 A2 | 5/2003 |
| WO | WO 2006/132850 A2 | 12/2006 |
| | (Continued) | |

OTHER PUBLICATIONS

European Patent Application No. 13275052.2-1506, European International Search Report, Berlin, Germany, Aug. 13, 2013, 9 pp.

*Primary Examiner* — Robert Lynch
(74) *Attorney, Agent, or Firm* — Brinks Gilson & Lione (57) ABSTRACT

A medical balloon (10) of a balloon catheter assembly (70) includes a balloon wall (22) formed of at least two layers (30, 32). The first layer (30) is made of an impervious polymeric material. The second layer (32), which is integral with the first layer (30) is made of a radiopaque and/or echogenic material and a polymeric material. In the preferred embodiment, there is provided 60 to 80% by weight of radiopaque material in the second layer (32). It has been found that these concentrations of radiopaque material provide good visibility of the balloon under ultrasonic imaging.

19 Claims, 8 Drawing Sheets

(56) References Cited

U.S. PATENT DOCUMENTS

| | | | |
|---|---|---|---|
| 5,195,969 A * | 3/1993 | Wang | A61M 25/1029 604/103 |
| 5,300,048 A | 4/1994 | Drewes, Jr. et al. | |
| 5,797,877 A * | 8/1998 | Hamilton et al. | 604/96.01 |
| 5,807,327 A * | 9/1998 | Green | A61F 2/958 604/194 |
| 5,948,489 A | 9/1999 | Hopkins | |
| 6,540,721 B1 | 4/2003 | Voyles et al. | |
| 6,652,568 B1 * | 11/2003 | Becker et al. | 604/96.01 |
| 6,761,708 B1 | 7/2004 | Chiu et al. | |
| 2004/0181252 A1 | 9/2004 | Boyle et al. | |
| 2007/0142771 A1 * | 6/2007 | Durcan | A61F 2/958 604/103.06 |
| 2008/0021495 A1 | 1/2008 | Lee et al. | |
| 2008/0045893 A1 | 2/2008 | Aita et al. | |
| 2009/0306589 A1 | 12/2009 | Tilson et al. | |
| 2009/0306769 A1 | 12/2009 | Schewe et al. | |
| 2011/0160661 A1 * | 6/2011 | Elton | 604/103.06 |

FOREIGN PATENT DOCUMENTS

| WO | WO 2007/056058 A2 | 5/2007 |
|---|---|---|
| WO | WO 2009/080320 A1 | 7/2009 |
| WO | WO 2010/027998 A1 | 3/2010 |

\* cited by examiner

MEDICAL BALLOON AND BALLOON CATHETER ASSEMBLY

CROSS-REFERENCE TO RELATED APPLICATIONS

This application claims priority to GB application No. 1114703.0, filed Aug. 25, 2011, titled "Medical Balloon and Balloon Catheter Assembly", the contents of which are incorporated herein by reference.

TECHNICAL FIELD

The present invention relates to a balloon catheter assembly for medical applications and in particular to an assembly which includes a radiopaque and/or echogenic balloon. The invention also relates to a radiopaque and/or echogenic medical balloon per se.

BACKGROUND ART

Balloon catheters are in widespread use for effecting various medical treatments, including vascular dilatation, angioplasty, vascular occlusion and also for deploying implantable medical devices.

It is highly advantageous for the balloons of such assemblies to be made of a material and form that they can be wrapped or folded onto the carrier catheter to as small a diameter as possible. Moreover, it is important for such balloons to be made of a material which can withstand the pressures to which they are inflated and the rigors of the medical treatment. As a result of these requirements, medical balloons tend to be made of a thin and strong material. Examples include polyamide (e.g. nylon), polyether block amide (e.g. Pebax®), PET, polyethylene and polyurethane.

These materials form good balloon structures but are very difficult to detect when deployed in a patient. The use of fluoroscopy, X-rays or CRT techniques can improve the visibility of these balloons when in the patient's body but are not optimal techniques. Ultrasonic imaging is a medically preferred technique but not ideal for imaging balloons or balloon catheters, which are in some cases invisible. Attempts have been made to provide such balloons with an element which gives them echogenicity or radiopacity. A common route is to use contrast media to inflate the balloon. While contrast media does enable the balloon to be readily visible by ultrasonic imaging, this is only once the balloon has been inflated; with no contrast media the balloon remains invisible. Moreover, contrast media is relatively viscous, which results in slower inflation and deflation times and also in a limit to the minimum diameter of the inflation and/or deflation lumen which can be used for injecting and/or removing the contrast media into or from the balloon. This also dictates a minimum size of catheter which can be used with these arrangements. Furthermore, contrast media is not particularly biocompatible, leading to risks of medical complications should there occur loss of contrast media into the patient's body, for instance as a result of balloon burst.

Balloon catheter assemblies which include one or more radiopaque and/or echogenic features have been disclosed in U.S. Pat. No. 3,228,894, U.S. Pat. No. 4,702,252, U.S. Pat. No. 5,300,048, U.S. Pat. No. 5,948,489, U.S. Pat. No. 6,540,721, U.S. Pat. No. 6,652,568, U.S. Pat. No. 6,761,708, US-2004/181,252, US-2008/045,893, US-2009/306,589 and US-2009/306,769.

DISCLOSURE OF THE INVENTION

The present invention seeks to provide an improved balloon catheter assembly and an improved medical balloon.

According to an aspect of the present invention, there is provided a medical balloon for endoluminal location within a patient, the balloon including a first balloon layer made of impervious polymeric material, and a second balloon layer integral with the first balloon layer, which second balloon layer includes a combination of radiopaque and/or echogenic material and polymeric material.

This structure provides for the balloon itself to include within it a radiopaque and/or echogenic material. However, as many radiopaque and/or echogenic materials reduce the strength of the balloon wall, the structure taught herein provides a complete balloon layer or wall made of a polymeric material which gives strength and stability to the overall balloon. The radiopaque and/or echogenic material is contained in a second layer which also includes a polymeric material to ensure good bonding and integrity of the two balloon layers.

As a result of this structure, it is not necessary to use contrast media to inflate the balloon, although this is not excluded. Contrast media could nevertheless be used, for instance in a fluid with a lower concentration of contrast media than prior art arrangements.

In addition, the taught structures make the balloon visible at all its stages of its deployment and in particular enable the balloon to be seen even when it is deflated. This is particularly advantageous for ensuring accurate placement of the balloon at the treatment site.

Advantageously, the first balloon layer is made solely of polymeric material. This ensures that the first balloon layer can have optimal strength and performance characteristics.

It is most preferred that the first and second balloon layers are coextruded. By coextrusion of the layers a unitary balloon structure is provided. Coextrusion is possible by the provision of polymeric material in both of these balloon layers.

During coextrusion the two balloon layers are molten, drawn out side by side one another, and compressed together to form a single balloon wall. As the balloon structure cools and solidifies the polymer chains of the two layers may mix at the boundary between the layers, so that the balloon wall solidifies effectively as a unitary piece. The two balloon layers may be effectively two sub-layers of a single balloon wall. By coextruding the two balloon layers to form a balloon, the bonding between the layers is extremely strong, as if the balloon were one layer. Coextrusion of the balloon layers thus provides a particularly strong balloon structure which is resistant to bursting and tearing.

The second balloon layer may be fused or bonded to the first balloon layer. The second balloon layer may overlie the first balloon layer or may be inside the first balloon layer. The second balloon layer may be disposed concentrically within the first balloon layer. The first, polymeric balloon, layer takes the pressure of the inflation fluid, typically being the stronger of the two layers. The second, radiopaque and/or echogenic balloon layer, which is generally the weaker of the two layers, is supported by the first layer. When the second layer overlies the first layer, the second layer can act as a coating, protecting the inner layer from being torn or cut by features of the patient's anatomy, such as vascular plaque and the like.

Advantageously, the balloon is wrappable, preferably in the same manner and as readily as conventional medical balloons.

The radiopaque and/or echogenic material is preferably one or more of: tungsten, gold, platinum, palladium, barium or bismuth. Barium and bismuth are radiopaque; whereas tungsten, gold, platinum and palladium are both radiopaque and echogenic. Echogenic materials include PVC and fluoropolymers. These materials thus can provide good radiopacity, and/or echogenicity, and are biocompatible. Tungsten is the most preferred material as this has very good performance even when used in small amounts. Materials which are solely echogenic can be seen by fluoroscopy techniques.

The second balloon layer may include between 50 and 90% by weight of radiopaque/echogenic material. This is possible by virtue of the fact that the balloon includes a first layer of polymeric material which provides strong support to the radiopaque and/or echogenic layer.

Preferably, the second balloon layer includes between 60 and 80% by weight of radiopaque and/or echogenic material, more preferably substantially 65%, 70% or 80% by weight of radiopaque and/or echogenic material. Where the second layer contains between 60 and 80% by weight of radiopaque and/or echogenic material the balloon may be suitably strong for use in medical applications. In this case the effect of the reduction in strength of a balloon by inclusion of radiopaque material may be overcome by the inclusion within the balloon wall of the first balloon layer made of impervious polymeric material. Where the balloon layers are coextruded the stronger first balloon layer is strongly bonded to/integrated with the second weaker layer, providing a balloon structure which is suitably strong for medical use.

A layer with 60-80%, in particular 80%, of tungsten has been found to be particularly visible, for example using fluoroscopy and ultrasound.

In terms of concentration by volume, the radiopaque/echogenic material may comprise substantially 11.4% to substantially 20.6%, substantially 13.7% to substantially 18.3%, or substantially 14.8% to 18.3% by volume.

In an embodiment, the second balloon layer includes a mix or blend of radiopaque/echogenic material and polymeric material.

Advantageously, the first balloon layer is made of a blend of polymers. The second balloon layer may similarly include a blend of polymers.

It is preferred that the polymeric materials of the first and second balloon layers are the same. This ensures a strong and unitary coupling of the two layers to one another, and in some instances at least a seamless interface between the two layers.

In another embodiment, the polymeric materials of the first and second balloon layers are different.

The polymeric material of the first and/or the second balloon layer may include one or more of polyamide, polyether block amide (Pebax®), PET, polyethylene and polyurethane.

It is preferred that the second balloon layer covers the entirety of the balloon, in some embodiments the second balloon layer may cover the entirety of an inflatable portion of the balloon, and in other embodiments the second balloon layer may cover the entirety of the balloon and at least a portion of the catheter.

It is envisaged that the radiopaque and/or echogenic material may be in the form of a powder or particulates combined with polymeric material, having for example an average diameter of less than 100 micrometers such as 40 or 50 micrometers or less. The radiopaque material may be in the form of particulates of average diameter of around or less than 10 micrometers. The radiopaque material may be in the form of particulates of average diameter of around or less than 5 micrometers. In one embodiment the particulates have an average diameter of around or less than 2 micrometers, such as 1.6 µm±0.2 µm.

The balloon layers may have a thickness in the range of 0.03 millimeters to 0.35 millimeters. The balloon layers preferably have a thickness in the range of 0.05 millimeters to 0.35 millimeters for a balloon of around 1.4 to 2.1 mm in diameter.

In some embodiments, there is provided a third balloon layer overlying the second balloon layer. The third balloon layer may be made from the same polymeric material as the first balloon layer. The third balloon layer may be coextruded with the first and second layers.

According to another aspect of the invention a method of manufacturing a medical balloon for endoluminal location within a patient, the balloon including a first balloon layer made of impervious polymeric material, and a second balloon layer integral with the first balloon layer, which second balloon layer includes a combination of radiopaque and/or echogenic material and polymeric material, whereby the medical balloon is echogenic and/or radiopaque, the method comprising:

coextruding the first and second balloon layers.

BRIEF DESCRIPTION OF THE DRAWINGS

Embodiments of the present invention are described below, by way of example only with reference to the accompanying drawings, in which.

DESCRIPTION OF THE PREFERRED EMBODIMENTS

In the drawings and examples which follows, there are shown and described various embodiments of medical balloon which can be used for vessel dilatation and for occlusion purposes. The balloons could also be used for deploying implantable medical devices, such as stents, stent grafts and so on. It is also envisaged that the balloons could be used for angioplasty procedures, in which case the balloons would typically be provided with one or more scoring or cutting elements of a type known in the art and which may typically be attached to the outer surface of the balloon or be provided in the form of ribs extending radially beyond the outer surface of the balloon.

Figure 1:
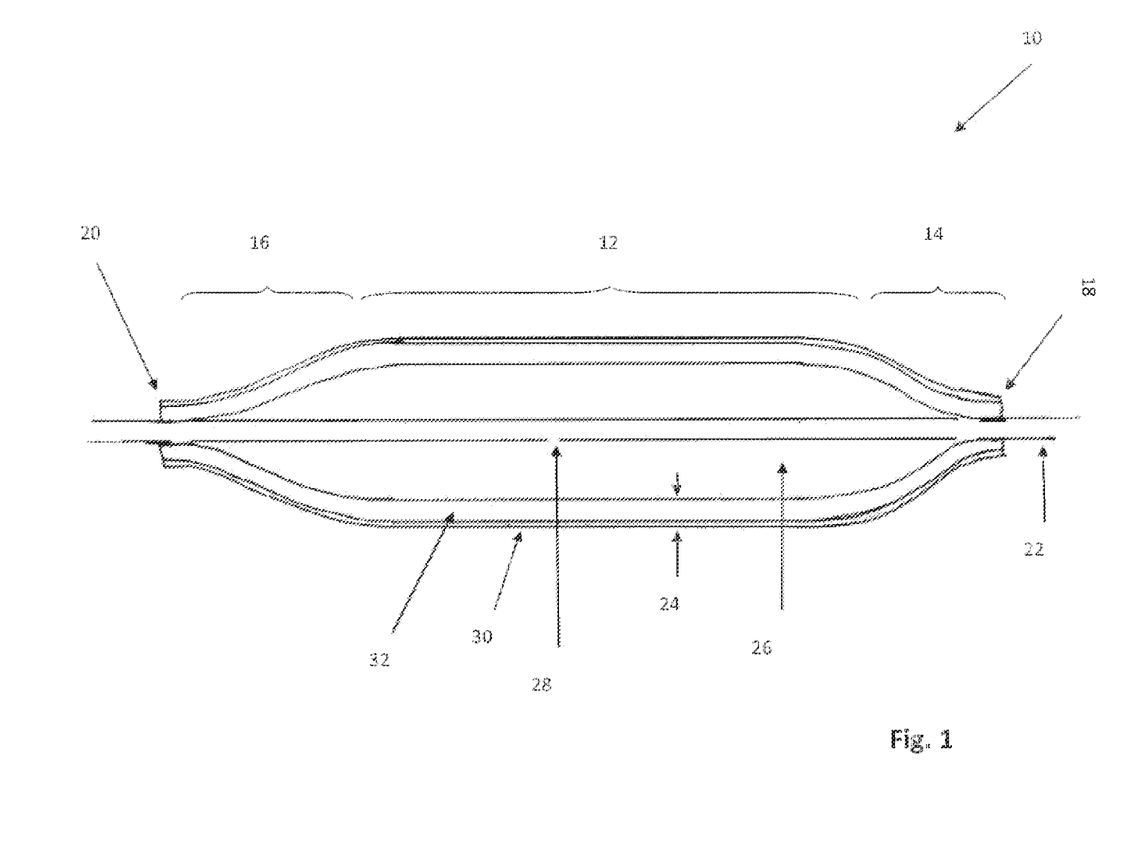
FIG. 1 is a cross-sectional view in side elevation of an embodiment of medical balloon for a balloon catheter assembly.

Referring now to FIG. 1, there is shown in cross-section a first embodiment of medical balloon 10. The balloon 10, in this example, is of conventional form and includes a central body portion 12 which is substantially cylindrical and of generally uniform radius along its length. Bounding the two ends of the body portion 12 are conical end portions 14, 16 which extend to necks 18, 20, the latter being fixed in fluid tight manner to a balloon catheter 22. The necks 18, 20 can be fixed to the catheter 22 in any conventional manner commonly used in the art.

The balloon 10 has a balloon wall 24 which provides therewithin a chamber 26 into which fluid can be fed to expand or deploy the balloon 10 and out of which fluid can be removed to collapse the balloon 10. For this purpose, the balloon catheter 22 is provided with at least one port 28 to which fluid can be fed into or taken from the chamber 26 of the balloon 10. The balloon catheter 22 is also provided, as is known in the art, with one or more lumens for the supply of inflation/deflation fluid.

The balloon wall 24 is made of a material which provides the balloon with flexibility and which is also relatively strong in order to withstand inflation the typical pressures required in the use of the balloon 10 and also to minimise, as far as possible, any damage to the balloon 10 during its use, in particular to minimise the risk of the balloon burst or tearing. For this purpose, the wall of the balloon may be made of or include a polyamide (such as nylon, preferably nylon 12), polyether block amide (Pebax), PET, polyethylene or polyurethane. The balloon wall 24 may include one or more of these materials, either in separate layers or in blends, and it is not excluded that other suitable balloon materials could be used or included. The wall 24 is such as to be wrappable around the balloon catheter 22 for deployment purposes, as is known in the art.

In the embodiment shown in FIG. 1, the balloon wall 24 is formed of two layers, a first balloon layer 30 which is made of an impervious polymeric material and a second balloon layer 32 which, in this embodiment, is located concentrically inside the first balloon layer 30, thereby to be on the inside of the layer 30 when viewed from the chamber 26 of the balloon 10. In other embodiments the second balloon layer 32 may overlie the first balloon layer, in which case, the second balloon layer may also be the outermost layer of the balloon 10, that is, with no other layer or coating overlying the second layer 32.

The second balloon layer 32 is made of a combination of radiopaque and/or echogenic material and a polymeric material. The first and second balloon layers 30, 32 are integral with one another and thereby in use behave as a unitary or singular balloon wall.

The second balloon layer 32 can include one or more of: tungsten, gold, platinum, palladium, barium or bismuth. These materials provide good radiopacity and/or echogenicity and are also biocompatible. Tungsten is the most preferred material as it provides very good radiopacity and/or echogenicity even when used in relatively small amounts. The inventors have discovered that with this arrangement, it is not necessarily the amount of radiopaque/echogenic material which is important in order to provide the balloon 10 with sufficient radiopacity and/or echogenicity to be seen during imaging, but it is the concentration of radiopaque/echogenic material which is provided. A high concentration of such materials creates a layer which has relatively low strength, particularly low resistance to tearing or bursting as a result of the pressure of the inflation fluid within the chamber 26.

The radiopaque and/or echogenic material which is included in the second layer 32 is blended with a polymeric material, which in the preferred embodiment is the same material as that of the first balloon layer 30. In the other embodiments, however, the second balloon layer 32 may comprise one or more different polymeric materials from the polymeric materials used for the first balloon layer and in particular polymeric materials which have a lower melting or softening temperature than that of the first balloon layer 30.

The proportion of radiopaque and/or echogenic to polymeric material of the second balloon layer 32 can typically be between 50 to 90% by weight. It has been found that a concentration within this range provides good radiopacity of the balloon 10 when viewed through ultrasonic imaging passed through a patient. It is preferred that the concentration of radiopaque material is between 60 to 80% by weight of material of the second balloon layer 32. It has been found that this provides a good balance between effective radiopacity and adequate strength of the second balloon layer 32. Tests have been carried out with concentration levels of 65 and 80% by weight which have been found to be particularly effective. A preferred formulation includes in the region of 80% of tungsten by weight. As explained, it has been found that it is the concentration of radiopaque material which provides the optimum characteristics in terms of radiopacity.

In terms of concentration by volume, the radiopaque/echogenic material may comprise substantially 11.4% to substantially 20.6%, more preferably substantially 13.7% to substantially 18.3%, most preferably 14.8% to 18.3% by volume.

It is to be appreciated that in the drawings, the components of the assembly as shown in exaggerated form for the sake of clarity of description. It will be appreciated that in practice the components, in particular the thickness of the walls or layers of the balloon, would be much less than shown in the drawings and equally in most instances the diameter of the balloon catheter would also be substantially less.

In the embodiment shown in FIG. 1, the first balloon layer 30 may have a thickness of between 0.02 to 0.1 millimeters, the second balloon layer a thickness of between 0.28 millimeters to 0.35 millimeters. The example shown includes an inner or second balloon layer of around 0.32 mm±0.03 mm, an outer or first balloon layer of 0.05 mm±0.015 mm, the balloon having an internal diameter in the region of 1.7 mm±0.05 mm.

These dimensions can vary, primarily in dependence upon the diameter of the balloon 10, the pressure at which the balloon 10 is intended to be operated, the medical treatment to be effected and the materials used for the various balloon layers.

It is preferred that the radiopaque and/or echogenic material is of a very fine particulate form which is thus able to mix or blend readily with the polymeric material of the radiopaque balloon layer. It is preferred that the polymeric material is made of particles of average diameter of less than 100 micrometers, more preferably of less than 40/50 µm. It is preferred, however, for the particulates to have a diameter much smaller than around 10 µm. In one embodiment they have an average diameter of around 2 µm or less.

Figure 3:
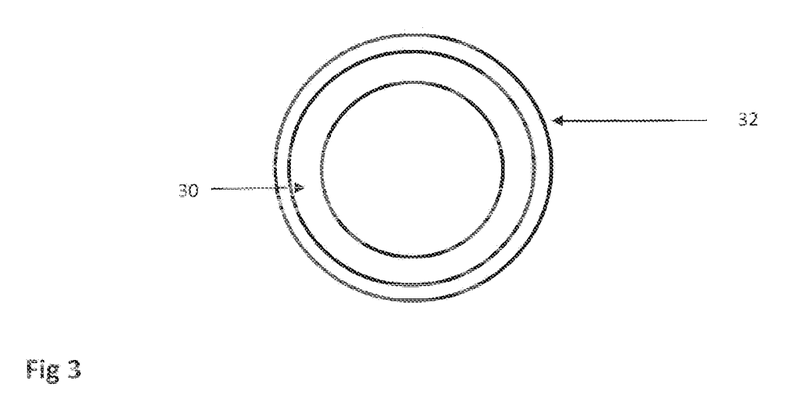
FIG. 3 is a transverse cross-sectional view of the embodiment of balloon of FIG. 1.
Figure 4:
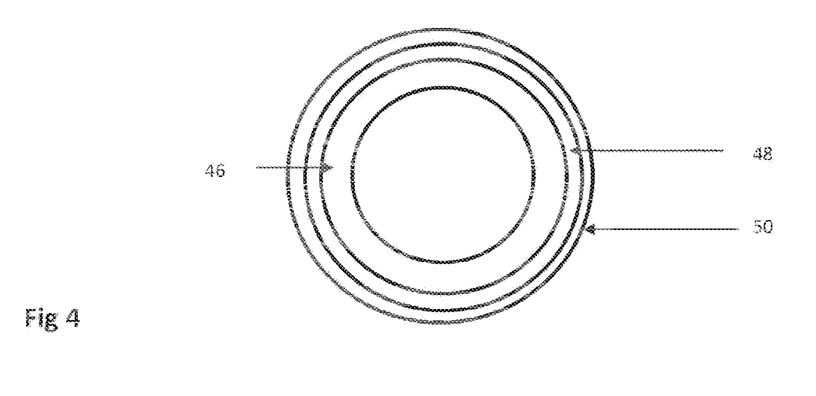
FIG. 4 is a transverse cross-sectional view of the embodiment of balloon of FIG. 2.

FIG. 3 shows a transverse cross sectional view of the embodiment of balloon of FIG. 1.

It will be understood that in the preferred embodiment the balloon wall 24, the individual balloon layers 30, 32 also, has a substantially uniform wall thickness, particularly over the body portion 12 of the balloon 10. In most embodiments, the balloon wall 24 and the individual layers of a balloon will have a uniform thickness throughout the length of the balloon. However, it is not excluded that this thickness may vary.

Figure 2:
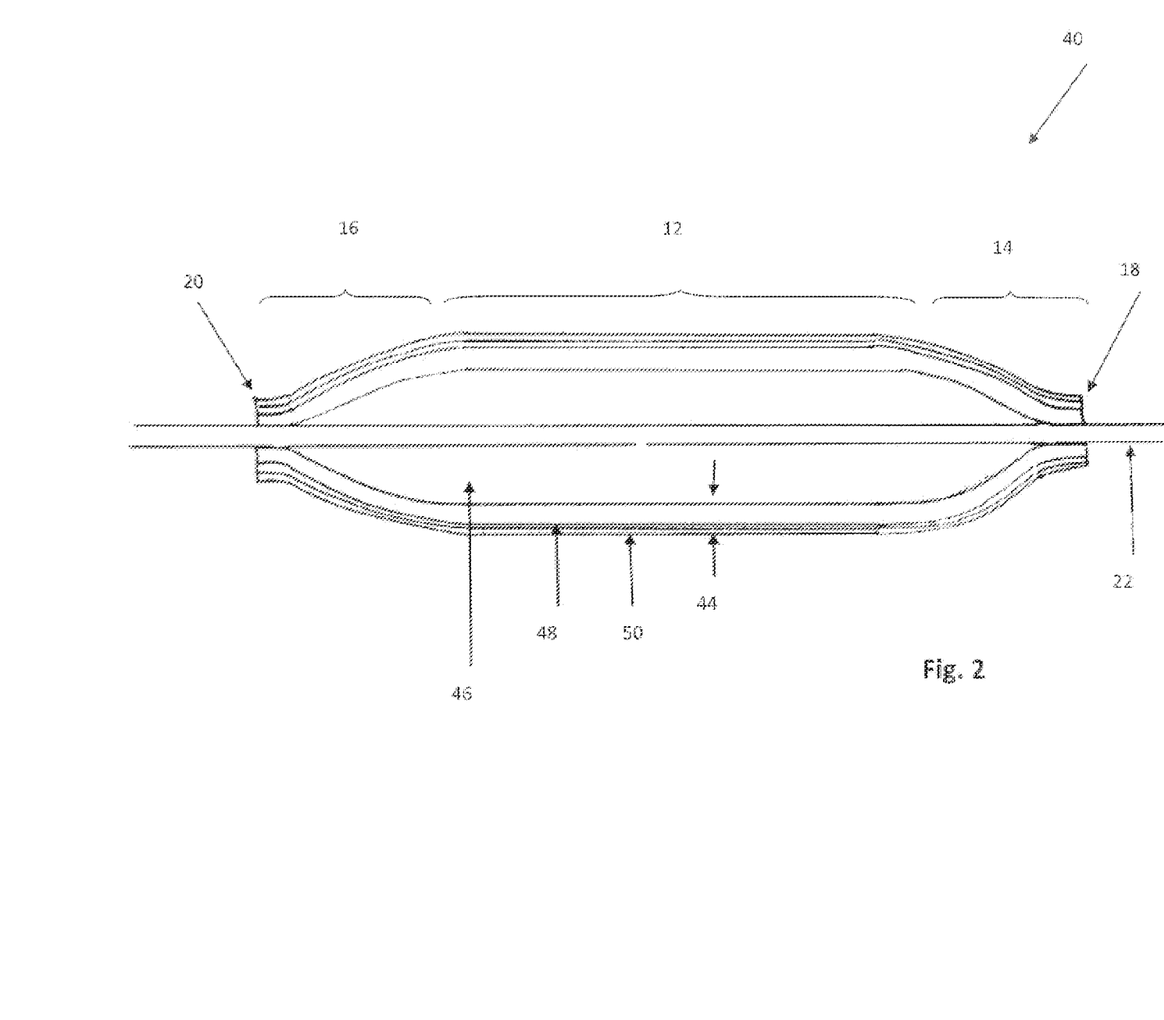
FIG. 2 is a cross-sectional view in side elevation of another embodiment of medical balloon for a balloon catheter assembly.

Referring now to FIG. 2, there is shown another embodiment of balloon 40 which is substantially similar in structure and form to the balloon 10 of the embodiment of FIG. 1. Balloon 40 includes a body portion 12 and first and second end cones 14, 16 ending at balloon necks 18, 20 fixed in fluid tight manner to the balloon catheter 22. The balloon includes a balloon wall 44 which is provided with a first balloon layer 46 made of impervious polymeric material and a second balloon layer 48 which includes a radiopaque and/or echogenic material combined with a polymeric material. In this regard, the first and second layers 46, 48 of the balloon 40 have similar characteristics and constituents, in at least one embodiment, to the balloon 10 of the embodiment of FIG. 1.

In this embodiment, the balloon wall 44 includes a third balloon layer 50 which overlies the second balloon layer 48 and which is made of a polymeric material, that is which does not have any radiopaque or echogenic material therein or at least any effective concentration of radiopaque or echogenic material. In the preferred embodiment, the first and third balloon layers 46, 50 are made of the same polymeric material but this is not essential. Indeed, the third or outer layer 50 could be made of a material which is not impervious, on the basis that the strength of the balloon 40 can be derived substantially entirely from the first or inner balloon layer 46.

The balloon layers 46, 48 and 50 can have any of the constituents disclosed herein.

In one embodiment, for a balloon of internal diameter in the region of 1.5 mm, the internal of first balloon layer 46 may have a thickness of around 0.13 mm±0.03 mm, the second, radiopaque/echogenic, balloon layer 48 a thickness in the region of 0.2 mm±0.03 mm and an outer balloon layer of around 0.15 mm±0.03 mm. As discussed above, these are merely exemplary.

Figure 5:
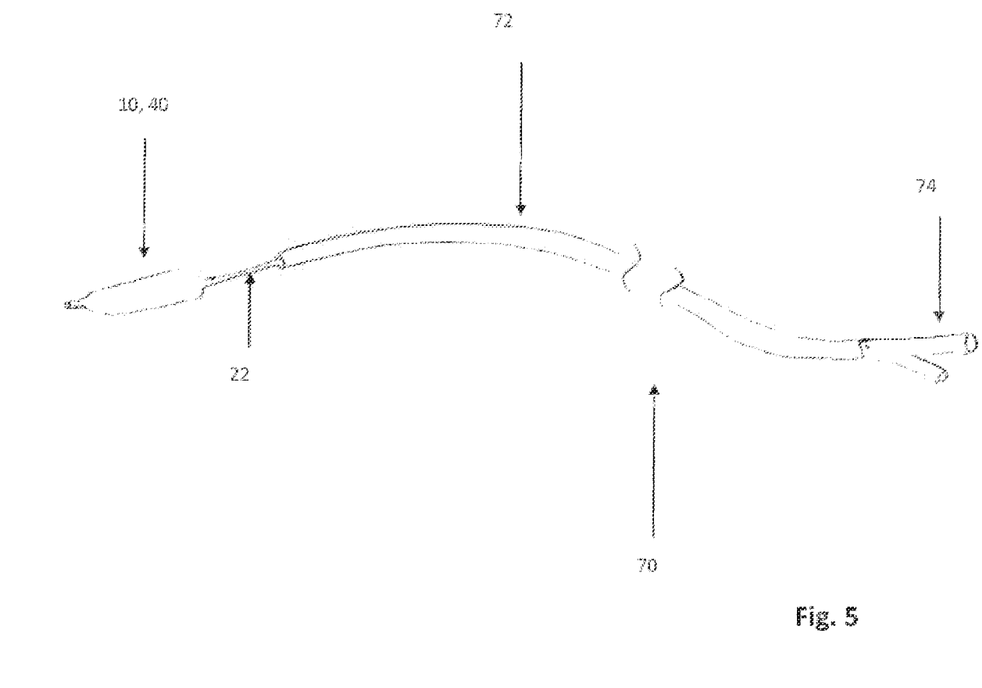
FIG. 5 is a schematic drawing of an embodiment of balloon catheter assembly.

FIG. 5 shows in schematic form an embodiment of balloon catheter assembly 70 which incorporates a balloon 10, 40 as disclosed herein. The assembly 70, which is generally of conventional form, includes an outer sheath 72 which is able to move reciprocally relative to the balloon catheter 22 and balloon 10, 40, from a withdrawn position shown in FIG. 5, in which the balloon 10, 40 is exposed, to a covering position in which it covers the balloon 10, 40, the latter being wrapped around the balloon catheter 22.

The assembly also includes a proximal unit 74 with one or more ports and associated couplings for feeding inflation/deflation fluid through suitable channels or lumens within the balloon catheter 22 to the balloon 10, 40 and also for the passage of a guide wire. As the balloon catheter assembly 70 is of generally well known form, it is not described in any further detail therein.

Figure 6:
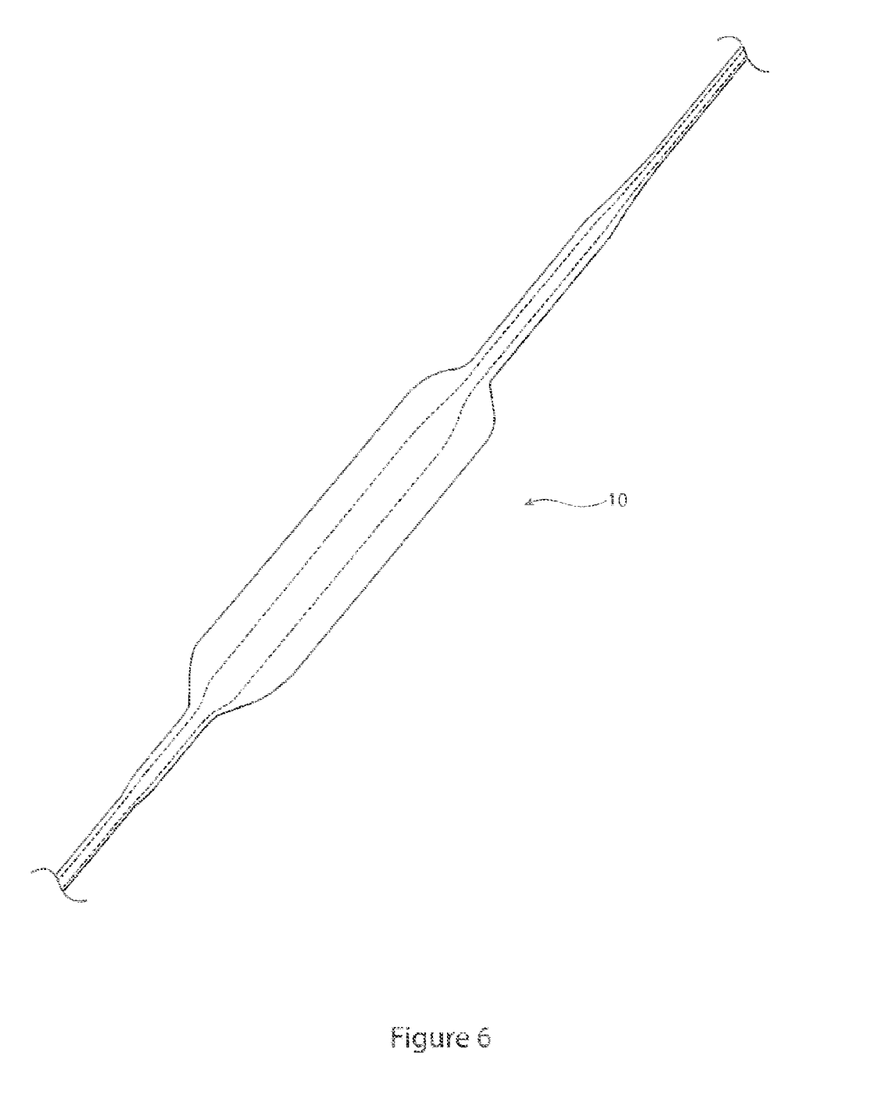
FIG. 6 is a photograph of an embodiment of radiopaque balloon.

Referring now to FIG. 6, there is shown a photograph of the preferred embodiment of the balloon, prior to cutting and fitting onto a balloon catheter 22. The balloon 10, in this example, is a two-layer balloon in which the outer layer is made of substantially 80% tungsten and 20% polymeric material (by weight). It has been found that this balloon is particularly visible in ultrasonic imaging.

Figure 7:
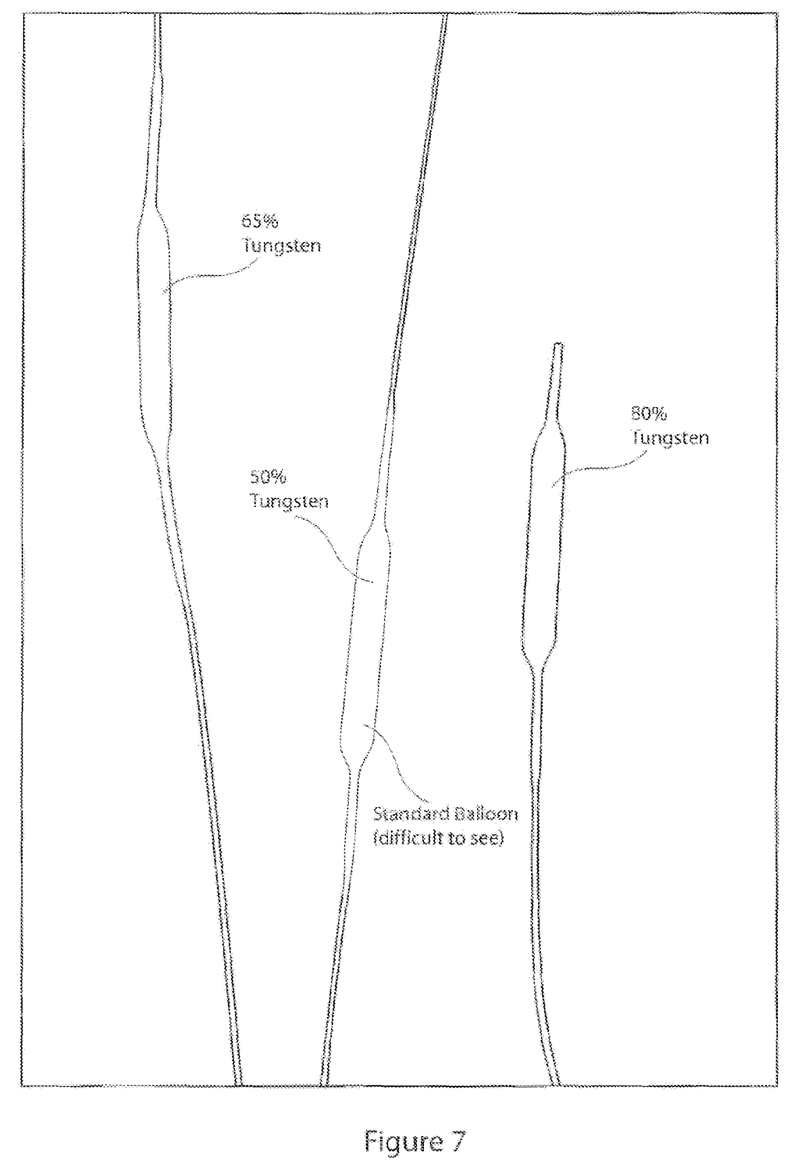
FIGS. 7 and 8 show fluoroscopic images of balloons with different amounts of radiopaque material within the second layer.
Figure 8:
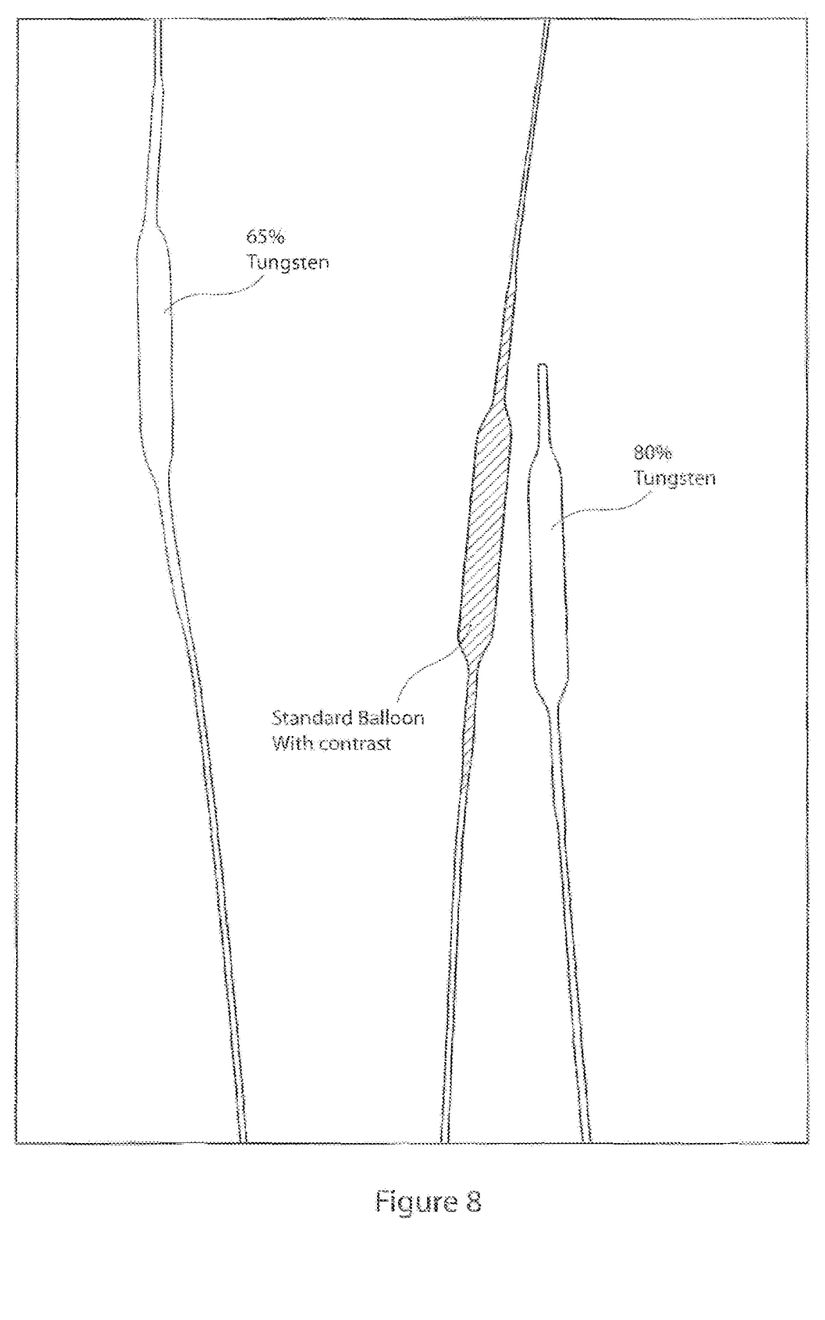

Referring to FIGS. 7 and 8 there is shown fluoroscopic images of balloons containing different amounts of radiopaque material within the second layer. In FIG. 7 a balloon comprising 50% by weight of tungsten in the second layer is barely visible, whereas balloons comprising 65% and 80% by of weight tungsten in the second layer are clearly visible. In FIG. 8 balloons comprising 65% and 80% by of weight tungsten in the second layer are shown with a balloon filled using contrast fluid.

Figure 9:
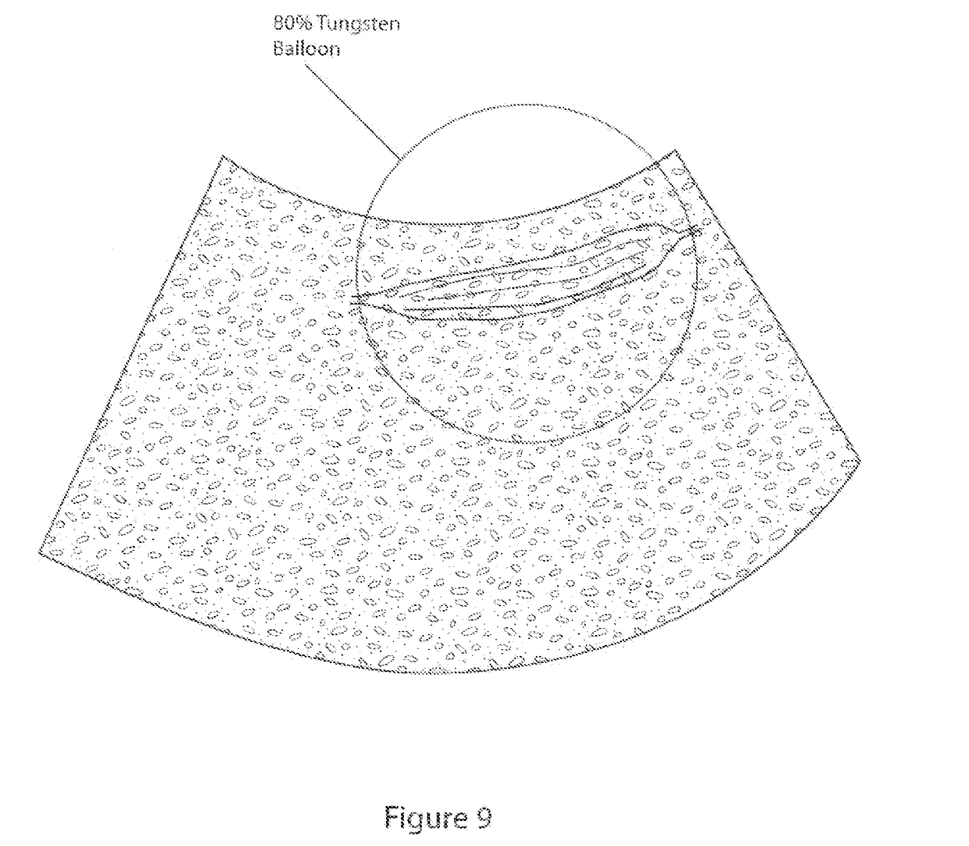
FIG. 9 shows an ultrasound image of a balloon with 80% by weight of tungsten in the second layer.

Referring to FIG. 9 there is shown an ultrasound image of a balloon with 80% by weight of tungsten in the second layer. The balloon is clearly visible in the ultrasound scan.

It will be appreciated from the above teachings that in the preferred embodiments the first or internal layer of the balloon 30, 46, is the layer which is made of impervious polymeric material and has no radiopaque or echogenic material therein, that is, made of pure polymeric material.

It has been explained above that the layer of imperious polymeric material, although preferably being the internal layer of the balloon 10, 40, could in the alternative be an outer layer of the balloon or an intermediate layer.

It is to be appreciated also that the balloon could have more than three layers.

The balloons shown in the drawings are substantially cylindrical, that is have a body portion 12 which is cylindrical. In some applications it may be desirable to have a balloon having a different shape, for instance a balloon in which the body portion 12 has an hourglass or waisted configuration. The teachings herein are applicable to balloons of any shape as well as, as mentioned above, balloons provided with other features such as cutting or scoring elements.

It is to be understood that only some embodiments are described above which would be apparent to the skilled person having regard to the teachings herein and that the described embodiments are not intended to be limiting of these teachings.

Although the claims are set out in single claim dependent form, it is to be understood that the claimed and disclosed features herein can be combined with one another and that the claims are intended to interpreted as covering these combinations as if they were in multiple dependent form.

The invention claimed is:

1. A medical balloon for endoluminal location within a patient, the balloon including a first balloon layer consisting of impervious polymeric material, and a second balloon layer integrally coextruded with the outside of the first balloon layer, which second balloon layer consists of a combination of radiopaque and/or echogenic material and polymeric material, the polymeric material of the first balloon layer and the polymeric material of the second balloon layer mixing at the boundary between the first balloon layer and the second balloon layer, the second balloon layer including between 60 and 80% by weight of metallic radiopaque and/or metallic echogenic material, whereby the medical balloon is echogenic and/or radiopaque, and wherein the polymeric materials of the first and second balloon layers are the same.

2. The medical balloon according to claim 1, wherein the balloon is wrappable.

3. The medical balloon according to claim 1, wherein the second layer includes radiopaque material of one or both of: barium and bismuth.

4. The medical balloon according to claim 1, wherein the second layer includes radiopaque and echogenic material of one or more of: tungsten, gold, platinum, palladium.

5. The medical balloon according to claim 1, wherein the second balloon layer includes substantially 65% or 80% by weight of radiopaque and/or echogenic material.

6. The medical balloon according to claim 1, wherein the second balloon layer includes a mix or blend of radiopaque and/or echogenic material and polymeric material.

7. The medical balloon according to claim 1, wherein the first balloon layer is made of a blend of polymers.

8. The medical balloon according to claim 1, wherein the second balloon layer includes a blend of polymers.

9. The medical balloon according to claim 1, wherein the polymeric material of the first and/or the second balloon layer includes one or more of nylon, polyether block amide, PET, polyethylene and polyurethane.

10. The medical balloon according to claim 1, wherein the second balloon layer extends over the entirety of the balloon.

11. The medical balloon according to claim 1, wherein the second balloon layer extends over the entirety of an inflatable portion of the balloon.

12. The medical balloon according to claim 1, wherein the second balloon layer extends over the entirety of the balloon and at least a portion of a catheter.

13. The medical balloon according to claim 1, wherein the radiopaque material is in the form of a powder or particulates combined with polymeric material.

14. The medical balloon according to claim 1, wherein the radiopaque material is in the form of particulates of average diameter of around or less than 10 micrometers.

15. The medical balloon according to claim 1, wherein the radiopaque material is in the form of particulates of average diameter of around or less than 5 micrometers.

16. The medical balloon according to claim 1, wherein the radiopaque material is in the form of particulates of average diameter of around or less than 2 micrometers.

17. The medical balloon according to claim 1, wherein the balloon layers have a thickness in the range of 0.03 millimeters to 0.35 millimeters.

18. A medical balloon for endoluminal location within a patient, the balloon including a first, inner balloon layer consisting of impervious polymeric material, a second, middle balloon layer integrally coextruded with the first balloon layer, and a third, outer balloon layer integrally coextruded with the second balloon layer and consisting of polymeric material, which second balloon layer includes a combination of radiopaque and/or echogenic material and polymeric material, the polymeric material of the first balloon layer and the polymeric material of the second balloon layer mixing at the boundary between the first balloon layer and the second balloon layer, the second balloon layer including between 60 and 80% by weight of radiopaque and/or echogenic material, whereby the medical balloon is echogenic and/or radiopaque, wherein the third balloon layer consists of the same polymeric material as the first balloon layer and as the polymeric material of the second balloon layer.

19. The medical balloon according to claim 18, wherein the polymeric material of the second balloon layer and the polymeric material of the third balloon layer mix at the boundary between the second balloon layer and the third balloon layer.

* * * * *